US006712798B2

(12) United States Patent
Constantz

(10) Patent No.: US 6,712,798 B2
(45) Date of Patent: Mar. 30, 2004

(54) MULTILUMEN CATHETERS AND METHODS FOR THEIR USE

(75) Inventor: Brent R. Constantz, Menlo Park, CA (US)

(73) Assignee: Corazon Technologies, Inc., Menlo Park, CA (US)

( * ) Notice: Subject to any disclaimer, the term of this patent is extended or adjusted under 35 U.S.C. 154(b) by 71 days.

(21) Appl. No.: 10/101,544

(22) Filed: Mar. 18, 2002

(65) Prior Publication Data

US 2003/0187411 A1 Oct. 2, 2003

(51) Int. Cl.[7] .............................................. A61M 25/00
(52) U.S. Cl. ....................... 604/284; 604/533
(58) Field of Search .............................. 604/39, 43, 48, 604/93.01, 264, 523, 533, 284

(56) References Cited

U.S. PATENT DOCUMENTS

| | | |
|---|---|---|
| 4,329,994 A | 5/1982 | Cooper |
| 4,445,892 A | 5/1984 | Hussein et al. |
| 4,573,966 A | 3/1986 | Weikl et al. |
| 4,601,701 A * | 7/1986 | Mueller, Jr. .................. 604/83 |
| 4,610,662 A | 9/1986 | Weikl et al. |
| 4,636,195 A | 1/1987 | Wolinsky |
| 4,655,746 A * | 4/1987 | Daniels et al. .............. 604/509 |
| 4,824,436 A | 4/1989 | Wolinsky |
| 4,838,881 A | 6/1989 | Bennett |
| 4,901,734 A | 2/1990 | Griffin et al. |
| 4,911,163 A | 3/1990 | Fina |
| 4,976,733 A | 12/1990 | Girardot |
| 5,059,178 A | 10/1991 | Ya |
| 5,090,960 A | 2/1992 | Don Michael |
| 5,149,330 A | 9/1992 | Brightbill |
| 5,167,623 A | 12/1992 | Cianci et al. |
| 5,167,628 A | 12/1992 | Boyles |
| 5,195,955 A | 3/1993 | Don Michael |
| 5,207,648 A | 5/1993 | Gross |
| 5,222,941 A | 6/1993 | Don Michael |
| 5,380,284 A | 1/1995 | Don Michael |
| 5,443,446 A | 8/1995 | Shturman |
| 5,462,529 A | 10/1995 | Simpson et al. |
| 5,542,937 A | 8/1996 | Chee et al. |
| 5,925,016 A * | 7/1999 | Chornenky et al. ...... 604/96.01 |
| 5,957,973 A * | 9/1999 | Quiachon et al. .......... 623/1.23 |
| 6,004,310 A | 12/1999 | Bardsley et al. |
| 6,013,068 A | 1/2000 | Spiegelhalter |
| 6,113,576 A * | 9/2000 | Dance et al. ........... 604/164.01 |

FOREIGN PATENT DOCUMENTS

| | | |
|---|---|---|
| WO | WO 00/03651 | 1/2000 |
| WO | WO 01/13985 | 3/2001 |
| WO | WO 01/15767 | 3/2001 |
| WO | WO 01/39783 | 6/2001 |
| WO | WO 01/70320 | 9/2001 |
| WO | WO 02/15958 | 2/2002 |

* cited by examiner

*Primary Examiner*—LoAn H. Thanh
(74) *Attorney, Agent, or Firm*—Bret E. Field; Bozicevic, Field & Francis

(57) ABSTRACT

Multilumen catheters are provided. The subject multilumen catheters include a proximal end and a distal end separated by a non-coaxial multilumen tube. The subject catheters are further characterized in that they include a multiport manifold at their proximal ends, where at least two of the ports of the multiport manifold may comprise luer valves. Also provided are systems for use in flushing a vascular site with fluid, usually at least two different fluids, where the subject systems are made up of two multilumen catheters according to the subject invention, where one of the catheters is inserted inside of the other. In addition, kits comprising various components of the subject systems, e.g., at least two different multilumen catheters, are provided. The subject multilumen catheters, systems and kits find use in a variety of different applications in which it is desired to flush a vascular site with at least one and preferably two different fluids, where particular applications of interest include the treatment of vascular lesions.

3 Claims, 6 Drawing Sheets

MULTILUMEN CATHETERS AND METHODS FOR THEIR USE

FIELD OF THE INVENTION

The field of this invention is atherosclerosis and related vascular conditions, and particularly catheter devices used for treating such conditions.

BACKGROUND OF THE INVENTION

The formation of plaques or lesions (atherosclerotic plaques or lesions), on vascular tissue, such as the inner surface of blood vessels, aortic valves, etc., is a major component of various vascular disease conditions. For example, plaques on heart related vascular structures, e.g., coronary artery intima, heart valves, etc., are often implicated in various heart disease conditions. Likewise, plaques or lesions present on the intima of peripheral vessels, e.g., arteries, are often implicated in various peripheral vascular disease conditions.

A variety of different protocols have been developed for treating diseases associated with the presence of vascular lesions or plaques. Such treatment methodologies generally involve mechanical removal or reduction of the lesion, and include: bypass surgery, balloon angioplasty, mechanical debridement, atherectomy, valve replacement, and the like. Despite the plethora of different treatment strategies that have been developed for the treatment of such vascular disease conditions, there are disadvantages associated with each technique, such as tissue damage, invasiveness, etc. For example, restenosis is a common complication that results in arteries in which lesions have been mechanically removed.

As such, there is continued interest in the development of new treatment protocols for the removal of vascular lesions from vascular tissue, as well as catheter devices that are used in such protocols.

Literature

U.S. Patents of interest include: U.S. Pat. Nos. 4,329,994; 4,838,881; 5,149,330; 5,167,623; 5,207,648; 5,542,937; 6,004,310; and 6,013,068. Also of interest are U.S. Pat. Nos.: 4,445,892; 4,573,966; 4,610,662; 4,636,195; 4,655,746; 4,824,436; 4,911,163; 4,976,733; 5,059,178; 5,090,960; 5,167,628; 5,195,955; 5,222,941; 5,380,284; 5,443,446; and 5,462,529. See also: WO 00/03651; WO 01/13985; WO 01/15767; WO 01/39783; WO 01/70320; and WO 02/15958; the disclosures of the priority documents of which are herein incorporated by reference.

SUMMARY OF THE INVENTION

Multilumen catheters are provided. The subject multilumen catheters include a proximal end and a distal end separated by an off-axis or non-coaxial multilumen tube. The subject catheters are further characterized in that they include a multiport manifold at their proximal ends, where at least two of the ports of the multiport manifold comprise a mechanism, e.g., a luer valve, for establishing a sealed fluid communication with the lumen of an external tubular member. Also provided are systems for use in flushing a vascular site with fluid, usually at least two different fluids, where the subject systems are made up of two multilumen catheters according to the subject invention, where one of the catheters is inserted inside of the other catheter in a nesting configuration. Catheters so-configured and filled with such fluids are included in the invention. In addition, kits comprising various components of the subject systems, e.g., at least two different multilumen catheters, are provided. In addition, systems comprising various components of the subject systems, e.g., at least two different multilumen catheters, are provided. The subject multilumen catheters, systems and kits find use in a variety of different applications in which it is desired to flush a vascular site with at least one and preferably two different fluids, where particular applications of interest include the treatment of vascular lesions.

BRIEF DESCRIPTION OF THE FIGURES

Each of the following figures provide examples diagrammatically illustrating aspects of the present invention.

DESCRIPTION OF THE SPECIFIC EMBODIMENTS

Figure 1A:
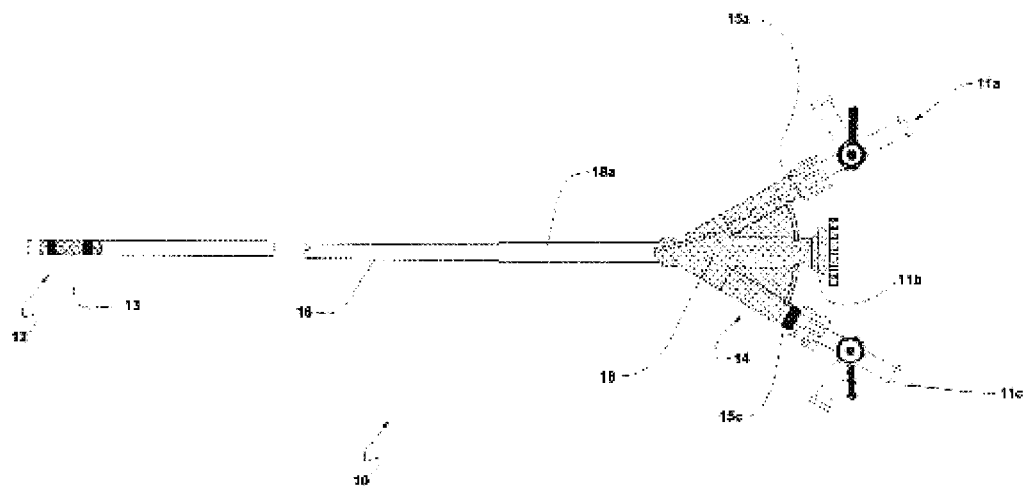
FIGS. 1A and 1B each provide a representation of an aspiration catheter according to the subject invention.

Multilumen catheters are provided. The subject multilumen catheters include a proximal end and a distal end separated by an off-axis or non-coaxial multilumen tube. The subject catheters are further characterized in that they include a multiport manifold at their proximal ends, where at least two of the ports of the multiport manifold comprise a mechanism, e.g., a luer valve, for establishing a sealed fluid communication with the lumen of an external tubular member. Also provided are systems for use in flushing a vascular site with fluid, usually at least two different fluids, where the subject systems are made up of two multilumen catheters according to the subject invention, where one of the catheters is inserted inside of the other catheter in a nesting configuration. Catheters so-configured and filled with such fluids are included in the invention. In addition, kits comprising various components of the subject systems, e.g., at least two different multilumen catheters, are provided. In addition, systems comprising various components of the subject systems, e.g., at least two different multilumen catheters, are provided. The subject multilumen catheters, systems and kits find use in a variety of different applications in which it is desired to flush a vascular site with at least one and preferably two different fluids, where particular applications of interest include the treatment of vascular lesions.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that, as used in this specification and the appended claims, the singular forms "a," "an" and "the" include plural reference unless the context clearly dictates otherwise. Unless defined otherwise all technical and scientific terms used herein have the same meaning as commonly understood to one of ordinary skill in the art to which this invention belongs.

Where a range of values is provided, it is understood that each intervening value, to the tenth of the unit of the lower limit, unless the context clearly dictates otherwise, between the upper and lower limit of that range and any other stated or intervening value in that stated range, is encompassed within the invention. The upper and lower limits of these smaller ranges may independently be included in the smaller ranges, and such embodiments are also encompassed within the invention, subject to any specifically excluded limit in the stated range. Where the stated range includes one or both of the limits, ranges excluding either or both of those included limits are also included in the invention.

All publications mentioned herein are incorporated herein by reference for the purpose of describing and disclosing components that are described in the publications that might be used in connection with the presently described invention.

Systems as introduced in the Summary of the Invention are described in detail below. The subject multilumen catheters will be described first, both generally and in terms of the figures, followed by a description of the subject systems, kits and representative methods in which the catheters, systems and kits find use.

Multilumen Catheters

As summarized above, the present invention provides multilumen catheters. Specifically, the subject invention includes three different multilumen catheters, which can be used together as a system to simultaneously flush a vascular site with two distinct fluids. Common features of each catheter of the subject invention are that they include a proximal end and a distal end separated by an elongated non-coaxial multilumen tube. By non-coaxial multilumen tube, it is meant a tube that includes at least two lumens which are non-coaxial, i.e., they do not share a common axis. The number of lumens in the multilumen tube may vary, but generally is 2 to 5, and is often 2 to 4, where in certain embodiments the number is 2 or 3. By elongated, it is meant that the distance between the proximal and distal ends is sufficient for the catheter to be inserted or introduced into the vascular system of a patient at a site remote from the vascular lesion that is to be treated through action of the distal end of the catheter, as is known in the art. Catheters intended for intravascular introduction will typically have a length in the range from 50 cm to 200 cm and an outer diameter in the range from 1 French (0.33 mm; Fr.) to 12 Fr., usually from 3 Fr. to 9 Fr. In the case of coronary catheters, the length is typically in the range from 125 to 200 cm, the diameter is preferably below 8 Fr., more preferably below 7 Fr., and most preferably in the range from 2 Fr. to 7 Fr. In certain embodiments, the elongated tubular element has a length of from about 80 to 200 cm, usually from about 90 to 180 cm and more usually from about 90 to 140 cm.

All of the subject multilumen catheters are further characterized in that they include a multiport manifold at their proximal ends. By multiport manifold is meant a manifold that includes two or more ports (in addition to the attachment structure of the mannifold to the proximal end of the elongated tube of the catheter), where the number of ports in the manifold may range from 2 to 4, but is generally 2 or 3, depending on the particular multilumen catheter. In addition, at least two of the ports of the multiport manifold preferably have luer valves or analogous means for establishing a sealed fluid communication with the lumen of an external tubular element or analogous fluid conveying means. In many embodiments, a luer valve is present in these ports, where the valve may be a male or female luer valve. Luer valves are disclosed in U.S. Pat. Nos. 6,063,062; 6,039,302; 5,954,313; 5,947,954; 5,788,215; 5,775,671; 5,738,144; 5,549,651; 5,535,785; 5,474,544; 5,441,487; 5,372,143; 5,284,475; the disclosures of which are herein incorporated by reference. As such, where the multiport manifold is a two port manifold, each of the two ports in the manifold will typically have a luer valve. Alternatively, where the multiport manifold is a three port manifold, only two of the three ports may have luer valves or all three ports may have luer valves.

Another common feature of all of the multilumen catheters of the subject invention is that the elongated multilumen tube is typically a polymeric extruded element, which is made up of one or more biocompatible polymers that have been extruded to produce the non-coaxial multilumen tube. Biocompatible polymers of interest include, but are not limited to: polyimide, polyamide, PBAX™, polyethylene, polyisoprene, nylon and the like.

Although each of the disparate multilumen catheters share the above common features, there are differences between the different specific multilumen catheter designs of the subject invention. As such, each specific type of multilumen catheter of the subject invention, e.g., aspiration, total and partial multilumen catheters, will now be described separately in greater detail.

Aspiration Catheter

The first multilumen catheter of the subject invention is identified herein as the aspiration catheter, as it includes the lumen employed for aspiration when the catheter is used in a system for flushing a vascular site with fluid. The aspiration catheter is characterized by having a proximal end and a distal end separated by a non-coaxial two lumen tube, where a three port manifold is present at the proximal end. In the three port manifold, two of the ports, and more specifically the side or offset ports, have luer valves, while the central port has a valve capable of opening and closing around a tubular element, e.g., a catheter, dilator, guidewire, etc., to produce a sealed relationship with the tubular element. In many embodiments, this element is a Touhy-Borst valve or analogous structure, where Touhy-Borst valves are described in U.S. Pat. Nos.: 5,795,307 and 5,320,613; the disclosures of which are herein incorporated by reference.

FIGS. 1A and B provide a depiction of a representative aspiration catheter according to the subject invention. In FIG. 1A, aspiration catheter 10 has proximal end 14 and distal end 12 separated by elongated non-coaxial two lumen tube 16. The length of elongated tube 16 should be long enough to provide for access of the distal end to the target vascular site upon introduction into the host, subject or patient at a remote site, and typically ranges from about 80 to 200 cm, usually from about 90 to 180 cm and more usually from about 90 to 140 cm. The outer diameter of the elongate tubular member 16 may vary depending on the target vascular site for which it is designed to be used. In other words, the outer diameter of the aspiration catheter is selected so as to provide for access of the distal end of the catheter to the vascular site via the vascular system from the remote point of entry, where the outer diameter typically ranges from about 1.0 to 4.0 mm (3 to 12 Fr), usually from about 1.5 to 3.0 mm (4.5 to 9.0 Fr) and more usually from about 1.7 to 2.7 mm (5 to 8 Fr). In the case of coronary catheters, the length is typically in the range from 125 to 200 cm, the diameter is preferably below 8 Fr., more preferably below 7 Fr., and most preferably in the range from 2 Fr. to 7 Fr.

Figure 1B:
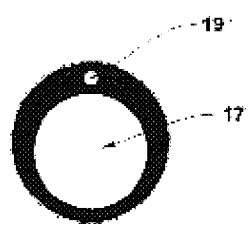

The aspiration catheter is further characterized in that one of the two lumens, generally the larger of the two lumens, opens at the distal end, thereby providing a fluid entry site for fluid from the target vascular site to flow into the lumen. In FIG. 1B, this larger lumen is designated 17. The inner diameter of this lumen at the open distal end and along the entire length of the tube 16 is sufficient to house either a partial or total occlusion multilumen catheter, as described in greater detail below, and remove fluid from the vascular site at the desired rate, e.g., a rate that provides for substantially isometric or isobaric pressure in the vascular site during treatment, through the resultant annular space. This larger lumen 17 is also known as the aspiration lumen. The inner diameter of the aspiration lumen 17, at least at its distal end and generally along the entire length of the aspiration catheter, is sufficient to provide for adequate flow into the lumen of the catheter, and sometimes ranges from about 0.20 to 2.0, usually from about 0.25 to 1.75 and more usually from about 0.35 to 1.5 mm.

Also present at the distal end of the aspiration catheter 10 is a vessel occlusion means 13, where the vessel occlusion means is usually an inflatable balloon. The balloon 13 is one that is inflatable to a volume sufficient to substantially occlude the vessel in which the aspiration catheter is positioned, e.g., by pressing against the intimal surface of the vessel in which the aspiration catheter is positioned. The inflated balloon diameter generally ranges from about 2 to 30 mm, usually from about 5 to 20 mm. The inflated balloon length typically ranges from about 10 to 30 mm, usually from about 15 to 20 mm. The balloon is in fluid or gaseous communication with an inflation lumen 19 which is the other lumen of the two lumen tube and runs the length of the aspiration catheter from the balloon to the proximal end, but does not open up at the distal end of the catheter. The inflation lumen typically has an inner diameter that ranges from about 0.1 to 0.5 mm, usually from about 0.2 to 0.4 mm. In certain embodiments, the aspiration catheter further includes a separate guidewire lumen (not shown). However, in many embodiments, a separate guidewire lumen is not present.

At the proximal end 14 of aspiration catheter 10 is three port manifold 18. Three port manifold 18 includes side or offset ports 11a and 11c, as well as central port 11b. One of the offset ports, e.g., 11a is in fluid communication with the smaller lumen 19 and is attached to a balloon inflation means, e.g., a syringe filled with gas or fluid, during use. The other offset port, e.g., 11c, is in fluid communication the larger aspiration lumen 17 and is attached to a source of negative pressure, e.g., a vacuum, during use. Offset ports 11a and 11c are further characterized in having or being in communication with luer valves 15a and 15c, respectively. In many embodiments, luer valves 15a and 15c are female luer valves. Central port 11b is in fluid communication with the aspiration lumen 17 and provides the point of access for the total and partial occlusion catheters, described in greater detail below. As such, in the manifold 18 of the aspiration catheter, two of the ports of the manifold, specifically the central port and one of the offset ports, are in fluid communication with the aspiration lumen 17. Central port 11b is characterized by the presence of Touhy-Borst valve 15b or an analogous structure. Touhy-Borst valves suitable for use in medical devices, e.g., catheters, are described in U.S. Pat. Nos. 5,320,613 and 5,795,307.

Also present on the catheter shown in FIG. 1A is a strain relief 18a. The strain relief protects the proximal end of tube 16 from damage and gives strength to the transition between the tube and manifold 18. The strain relieve locally increases the stiffness of tube 16 to provide a moderated step-wise increase in stiffness from the relatively more flexible tube to the stiffer manifold member. The length of the strain relieve may varies from 5 to 40 mm, but is usually 20 to 30 mm in length. Suitable materials for strain relief 18a include fluorinated ethylene-propylene or a similar medical grade polymer.

The embodiment shown in FIG. 1A includes three-way stop cocks attached to each of the offset ports. These provide for further control of fluid flow into the lumens of the device and/or the introduction of two separate fluids into the same lumen of the device, e.g., an imaging solution into the aspiration lumen and aspiration of fluid through the aspiration lumen, depending on the state of the three way stop-cock.

For convenience during use of the aspiration catheter, each of the ports of the three port manifold may be uniquely identified, e.g., color coded, so that it is readily apparent as to the element that the port should be connected during use of the device, e.g. vacuum source, balloon inflation means, etc. For example, one of the offset ports may have a yellow band, one may have a green band and one may have a red band, thereby uniquely identifying the ports of the three port manifold.

Total Occlusion Multilumen Catheter

Figure 6:
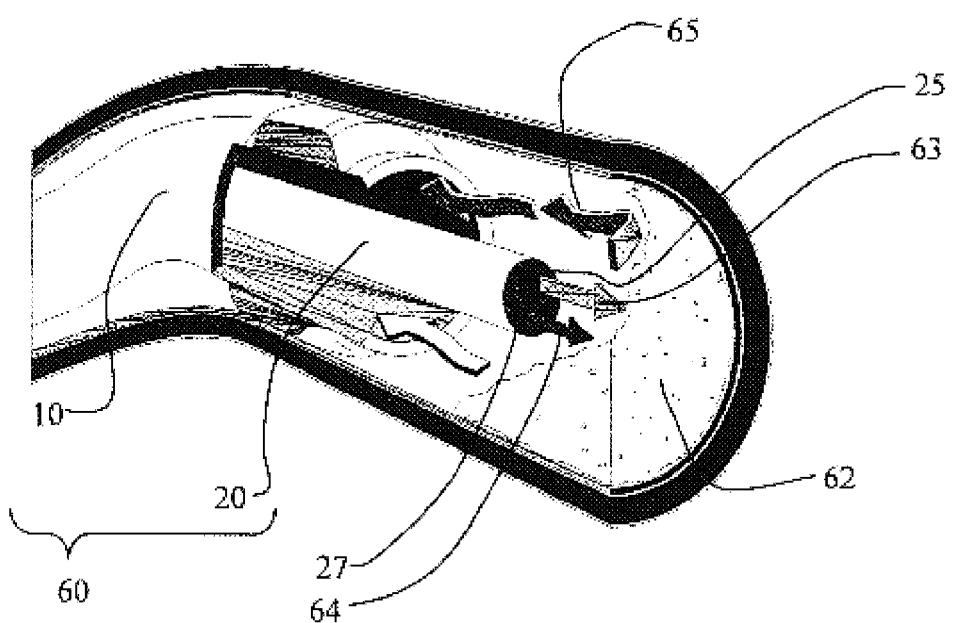
FIG. 6 shows the distal end of a total occlusion catheter system flushing a target vascular site in a method according to the subject invention.

Also provided by the subject invention are multilumen catheters that are designed to be inserted inside the aspiration lumen and used to flush a vascular site that is characterized by the presence of a total vascular occlusion, e.g., as shown in FIG. 6 described in greater detail below. These catheters are identified herein as total occlusion catheters. In general, the total occlusion catheters are characterized in that the multilumen tube separating the proximal and distal ends is a two lumen tube. These total occlusion catheters are further characterized in that the multiport manifold is preferably a two port manifold, where both of the ports have luer valves. In certain embodiments, the multilumen total occlusion aspiration catheter further includes a guidewire lumen.

Figure 2A:
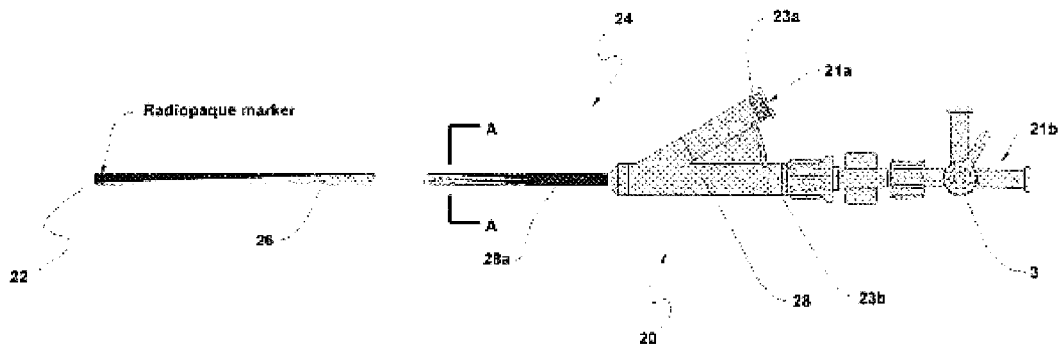
FIGS. 2A, 2B and 2C each provide a representation of a total occlusion catheter according to the subject invention.

FIGS. 2A and B and C each provide a representation of a total occlusion catheter according to the subject invention. As shown in FIG. 2A, total occlusion catheter 20 includes proximal end 24 and distal end 22 separated by elongated tubular member 26. Elongated tubular member 26 is sufficiently long to provide for access of the distal end to the target vascular site upon introduction into the host vascular system via a remote entry site of the vascular system. Typically, the length of elongate member 26 ranges from about 90 to 210 cm, usually from about 100 to 190 cm and more usually from about 110 to 150 cm. The outer diameter of the tubular member 26 is such that it may be slidably positioned inside the aspiration lumen of the aspiration catheter, as described above. Typically, the outer diameter of element 26 ranges from about 0.5 to 2.0 (1.5 to 6.0 Fr), usually from about 0.8 to 1.6 mm (2.5 to 5 Fr).

Figure 2B:
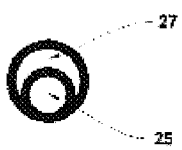
Figure 2C:

Tubular member 26 is a two lumen tubular member, where the lumens of the catheter are non-coaxial. Each of the lumens, 25 and 27, open at the distal end of catheter 20. One of the lumens is designed to carry a first fluid and the other is designed to carry a second fluid. In many embodiments, the first fluid is a dissolution fluid and the second fluid is a dissolution fluid attenuating fluid, as described in greater detail below. The configuration of the each of the lumens in the embodiment shown in FIG. 2A can be seen in FIG. 2B, which is a cross section of tubular member 26 taken at line A—A shown in FIG. 2A. As can be seen in the representative embodiment, lumen 25 has a substantially circular configuration while lumen 27 has a crescent configuration so as to share a common wall or border with a substantial portion of lumen 25, where by "substantial portion" is meant at least 25%, usually at least 35% and more usually at least 50% of the circumference of lumen 25, where in certain embodiments this portion may be much higher, e.g., 60%, 75% etc. Lumen 25 is typically employed for conveying the dissolution fluid while lumen 27 is typically employed for conveying the dissolution fluid attenuating fluid during use. In FIG. 2C, the cross sectional view show a three lumen total occlusion catheter, where lumen 25a is employed for dissolution solution, lumen 27 is employed for dissolution fluid attenuating fluid delivery and lumen 29 is the guidewire lumen.

The inner diameter of lumen 25 typically ranges from about 0.2 to 1.0 mm, usually from about 0.2 to 0.7 mm and more usually from about 0.3 to 0.4 mm, so as to provide for a cross-sectional area of about 0.03 to 0.8 mm$^2$, usually from about 0.03 to 0.4 mm$^2$ and more usually from about 0.07 to 0.2 mm$^2$. The cross-sectional area of lumen 27 typically ranges from about 0.03 to 0.8 mm$^2$, usually from about 0.03 to 0.4 mm$^2$ and more usually from about 0.07 to 0.2 mm$^2$. While the configuration of FIG. 2B shows a circular and crescent shaped lumen, other configurations are also possible, e.g., two circular lumens, to semicircular lumens, etc.

Also present on the preferred total occlusion catheter at proximal end 24 is two port manifold 28. Two port manifold 28 includes side or offset port 21a and central port 21b. Port 21a includes female luer valve 23a while port 23b includes high pressure female luer valve 23b. During use, side or offset port 21a is typically in fluid communication with a source of dissolution fluid attenuating fluid, e.g., buffer, while central port 23b is typically in fluid communication with a source of dissolution fluid, e.g., acid solution.

Also present on the catheter shown in FIG. 2A is a strain relief 28a. It functions as described in connection with strain relief 18a. In the embodiment shown in FIG. 2A, also present is three-way stop cock attached to the central port which provides for further control of fluid flow into the central lumens of the device, the introduction of two separate fluids into the same lumen of the device and/or the introduction of separate fluids for intermittent flushing, e.g., with heparinized saline, typically used to keep lumens clear and prevent clotting.

For convenience during use of the aspiration catheter, each of the ports of the two port manifold may be uniquely identified, e.g., color coded, so that it is readily apparent as to the element that the port should be connected during use of the device, e.g. dissolution fluid reservoir, dissolution fluid attenuating fluid reservoir, etc. For example, one of the offset ports may have a yellow band and one may have a red band, thereby uniquely identifying the ports of the manifold.

Partial Occlusion Catheter

Also provided by the subject invention are multilumen catheters that are designed to be inserted inside the aspiration lumen and used to flush a vascular site that is characterized by the presence of a partial vascular occlusion. These catheters are identified herein as partial occlusion catheters. In general, the partial occlusion catheters are characterized in that the multilumen tube separating the proximal and distal ends is a three lumen tube. These partial occlusion catheters are further characterized in that the multiport manifold is a three port manifold, where each of the ports has a luer valve or analogous structure. In addition to the above features, the partial occlusion catheter also includes a balloon or analogous vessel occlusion means at its distal end and multiple ports proximal to the balloon, where a portion of these infusion ports are in fluid communication with one of the lumens and the remainder are in fluid communication with another of the lumens. In certain embodiments, the partial occlusion catheters of the subject invention further include a guidewire lumen, bring the total number of lumens in the partial occlusion catheter to four.

Figure 3A:
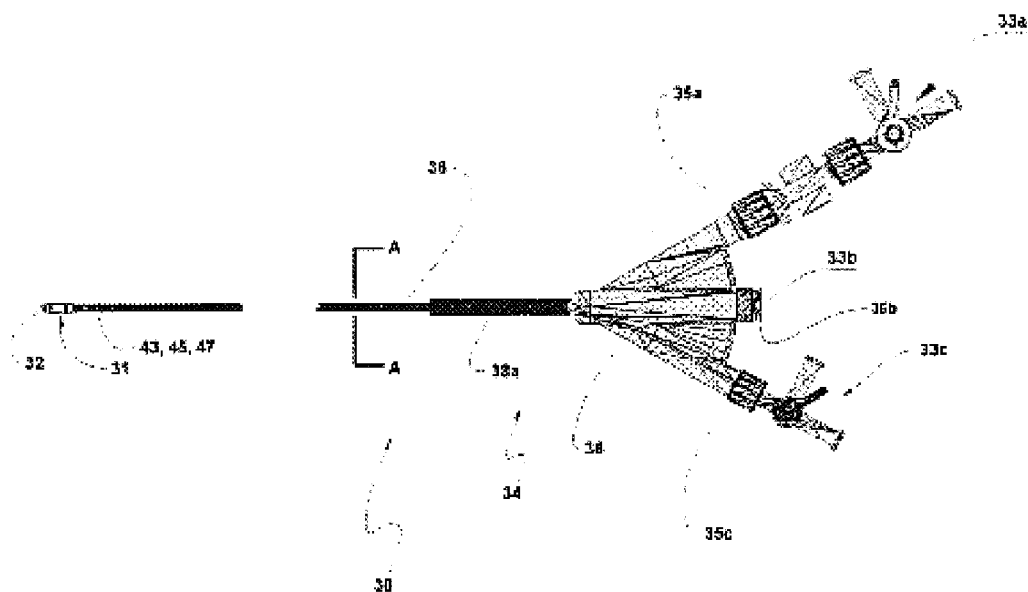
FIGS. 3A, 3B and 3C each provide a representation of a partial occlusion catheter according to the subject invention.

FIGS. 3A, B and C provide a representation of a partial occlusion catheter according to the subject invention. As shown in FIG. 3A, partial occlusion catheter 30 include sdistal end 32 and proximal end 34 separated by three lumen tube 36. The length of the tubular member 36 generally ranges from about 90 to 250 cm, usually from about 100 to 230 cm and more usually from about 110 to 190 cm. The outer diameter of the tubular member 36 is such that the partial occlusion catheter 30 may be slidably positioned in the aspiration lumen of the aspiration catheter. As such, the outer diameter of tubular member 36 typically ranges from about 0.5 to 2.0, usually from about 0.8 to 1.6 mm.

Located at the distal end of catheter 30 is balloon 31 or analogous occlusion means. The balloon is generally one that is inflatable to a diameter ranging from about 2 to 15 mm, usually about 5 to 10 mm, and typically has a length of from about 10 to 30 mm, usually from about 15 to 20 mm. Proximal to the balloon 31 are a series of ports 43, 45 and 47 which provide for fluid transfer between the outside of tube 36 and the lumens located inside the device. Typically, ports 43 and 45 are in fluid communication with a first lumen inside the tube 36 that is carrying dissolution fluid attenuating fluid while port 47 is in fluid communication with the lumen of the device carrying the dissolution fluid. The diameter of the infusion ports may vary, but typically ranges from about 0.2 to 1.2, usually from about 0.4 to 1.0 and more usually from about 0.5 to 0.8 mm.

Figure 3B:
Figure 3C:
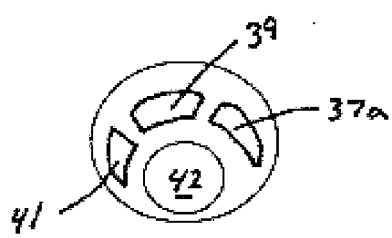

A representative configuration of the three lumens of multilumen tube 36 is shown in FIG. 3B, which shows the cross section of tube 36 taken along line A—A as shown in FIG. 3A. As shown in FIG. 3B, lumen 37 has a substantially circular cross section, while lumens 39 and 41 together make up a crescent shape that shares a border with lumen 37 that extends for a substantial portion of the perimeter of lumen 37. The crescent shape made through combination of lumens 39 and 41 is divided to provide for distinct lumens 39 and 41. The diameter of lumen 37 typically ranges from about 0.02 to 1.0 mm, usually from about 0.2 to 0.7 mm and more usually from about 0.3 to 0.4 mm to provide a cross-sectional area ranging from about 0.03 to 0.8 mm$^2$, usually from about 0.03 to 0.4 mm$^2$. The cross sectional area of lumen 39 typically ranges from about 0.03 to 0.8 mm$^2$, usually from about 0.03 to 0.4 mm$^2$ while the cross-sectional area of lumen 41 typically ranges from about 0.05 to about 0.3, usually from about 0.1 to about 0.2. In many embodiments, lumen 37 conveys dissolution fluid attenuating fluid, e.g., buffer, and/or provides for guidewire use, lumen 39 conveys dissolution fluid, e.g., acid, and lumen 41 conveys inflation medium, e.g., gas or fluid, to the balloon. While one type of configuration of the various lumens is shown, other non-coaxial configurations are also possible, e.g., three separate circles, a circle and two distinct crescent shapes, etc., where all of these potential configurations are within the scope of the invention. FIG. 3C provides a cross-section view of an embodiment that includes a guidewire lumen. As such, in FIG. 3C one can see the balloon lumen 41, the dissolution fluid and dissolution fluid conveyance lumens, 39 and 37a, as well as the guidewire lumen 42.

Located at the proximal end 34 of catheter 30 is three port manifold 38. Three port manifold 38 includes two offset or side ports 33*a* and 33*c*, which flank central port 33*b*. Each of the ports includes a female luer valve, 35*a*, 35*b* and 35*c*. The central port 33*b* is typically in fluid communication with a dissolution fluid attenuating fluid source during use. Offset port 33*a* is typically in fluid communication with a source of dissolution fluid. Offset port 33*c* is typically in fluid communication with a balloon inflation means, e.g., a syringe filled with a gas or liquid.

Also present on the catheter shown in FIG. 3A is a strain relief 38*a*. It functions in the manner of strain relief 18*a* and 28*a*.

In the embodiment shown in FIG. 3A, also present are three-way stop cocks attached to each of the offset ports, which elements provide for further control of fluid flow into the lumens of the device, the introduction of two separate fluids into the same lumen of the device and/or the introduction of separate fluids for intermittent flushing, e.g. with heparinized saline, typically used to keep lumens clear and prevent clotting, depending on the state of the three way stop-cock.

For convenience during use of the aspiration catheter, each of the ports of the three port manifold may be uniquely identified, e.g., color coded, so that it is readily apparent as to the element that the port should be connected during use of the device, e.g. vacuum dissolution fluid, dissolution fluid attenuating fluid, balloon inflation means, etc.

Systems

Also provided by the subject invention are systems for flushing a vascular site with two different fluids. By flushing a vascular site is meant introducing fluid into and removing fluid from a vascular site at substantially the same time such that the vascular site remains substantially stable in terms of pressure, e.g., is isobaric, where the pressure changes that occur in the vascular site do not exceed in magnitude a value of about 50 mm Hg and usually do not exceed about 30 mm Hg. Accordingly, maximum pressure will typically remain below about 400 mm Hg, preferably about 100 mm Hg.

Figure 4:
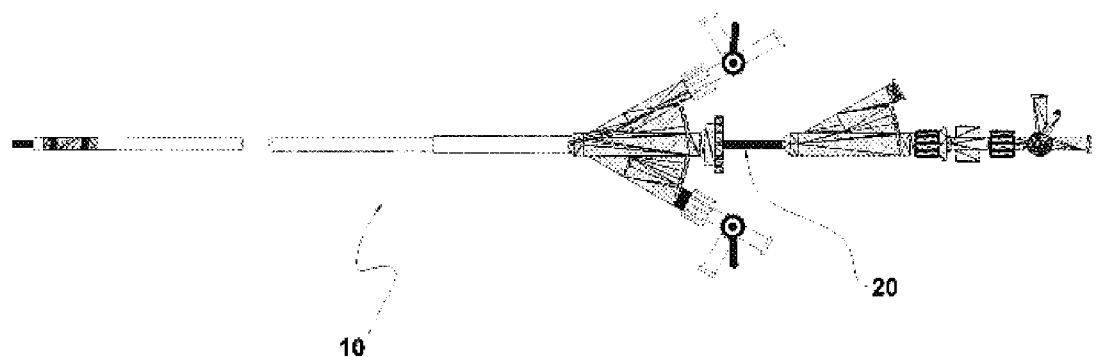
FIG. 4 provides a representation of a total occlusion catheter system according to the subject invention.
Figure 5:
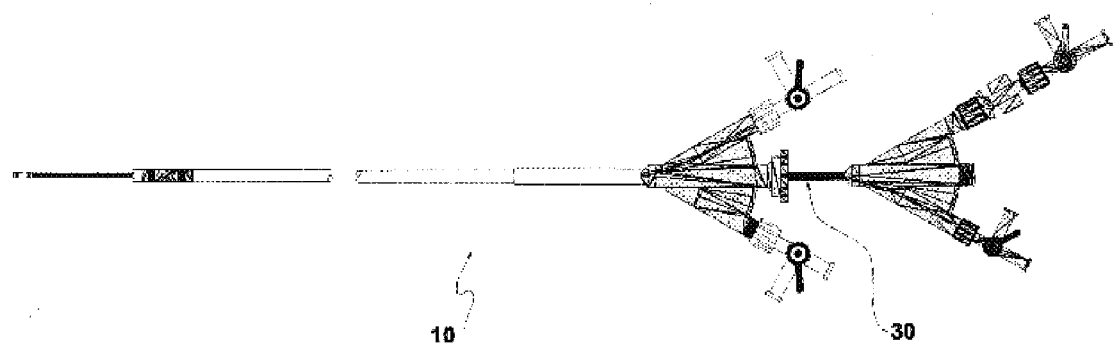
FIG. 5 provides a representation of a partial occlusion catheter system according to the subject invention.

The subject systems are characterized by having an aspiration catheter and one of the total or partial occlusion catheters of the subject invention in a nested configuration, such that the total or partial occlusion catheter is slidably positioned inside the aspiration lumen of the aspiration catheter. FIG. 4 provides a representation of a system designed for use with a total occlusion which is made up of a total occlusion catheter 20 inserted into the aspiration lumen of an aspiration catheter. FIG. 5 provides a representation of a system designed for use in the treatment of a partial occlusion, where the system is made up of a partial occlusion catheter inserted into the aspiration lumen of an aspiration catheter. Because the central manifold port of the aspiration catheter may have a Touhy-Borst valve, a fluid seal can be produced at the interface between the aspiration manifold central port and the outer surface of the partial or total occlusion catheter when inserted into the aspiration lumen of the aspiration catheter.

In using the total occlusion catheter system of the subject invention, one of the offset ports of the aspiration manifold is often in fluid communication with a syringe balloon inflation means and the other offset port of the aspiration manifold is in fluid communication with a vacuum source to provide the force for removing fluid from the vascular site via the aspiration lumen. The central port of the total occlusion manifold is in fluid communication with a source of dissolution fluid, e.g., an ENDoFLATOR®, etc., while the offset port of the total occlusion manifold is in fluid communication with a source of dissolution fluid attenuating fluid, e.g., an ENDoFLATOR®, etc.

In using the partial occlusion catheter system according to the subject invention, one of the offset ports of the aspiration manifold is often in fluid communication with a balloon inflation mechanism, e.g., a fluid or gas filled syringe, and the other offset port of the aspiration manifold is in fluid communication with a vacuum source. The central port of the partial occlusion manifold is in fluid communication with a source of dissolution fluid attenuating fluid, e.g., an ENDoFLATOR® filled with dissolution fluid attenuating fluid, while one of the offset ports is in fluid communication with a source of dissolution fluid, e.g. an ENDoFLATOR® filled with dissolution fluid, and the other offset port is in fluid communication with a balloon inflator, e.g. a fluid or gas filled syringe. In use, each of the catheters are filled with the respective solutions for which sources are provided. Furthermore, balloons provided will be at least partially filled, together with adjacent feed lumen in use. The aspiration lumen may also be subject to at least partial vacuum.

Methods

The subject systems find use in applications where it is desired to simultaneously flush a vascular target site with two different fluids. As mentioned above, by flush it is meant that the fluid is introduced into the vascular site and removed from the vascular site is accomplished in manner such that the vascular site remains at substantially constant pressure. However, the pressure throughout the treatment site is predicted to be, on average, lower than the backbleed pressure, i.e., the blood pressure on the proximal side of the aspiration catheter balloon. While the subject systems can, in principle, be employed to flush a vascular site with any two fluids, they are particularly suited for use in applications where chemical tissue ablation at a target vascular site is desired. As such, the subject systems find particular use in the treatment of vascular lesions or obstructions, where the target lesions or obstructions may be organic, inorganic or composite structures of both organic and inorganic components. In such embodiments, the systems are used to flush the target vascular site, and therefore the lesion or obstruction located therein, with a dissolution fluid and a dissolution fluid attenuating fluid.

In these embodiments of the subject methods, the first step is generally to provide for an entry site for the catheter into the vascular system of the host. Entry is typically provided by placement of an introducer sheath at a convenient location, e.g. leg etc., as is known in the art. A guidewire is then inserted through the entry sheath and its distal end is placed at the target vascular site. The aspiration catheter with a dilator present in the central lumen is then moved over the guidewire, where the guidewire generally passes through the central lumen, so that the distal end of the aspiration catheter reaches the target vascular site. Following placement of the distal end of the aspiration catheter at the target vascular site and subsequent deployment of the vascular occlusion means, the dilator is removed and replaced with either the partial or total occlusion catheter inserted through the Touhy-Borst valve of the aspiration manifold central port and into the aspiration lumen. This catheter insert is then moved through the lumen, optionally over the guidewire if still present, until the distal end of the insert is beyond the distal end of the aspiration catheter. In many embodiments, the distal end of the insert will extend some distance beyond the distal end of the aspiration catheter, where this distance typically does not exceed about 20 cm and usually does not exceed about 5 mm.

Upon positioning of the catheter system as described above and deployment of any vascular occlusion means, the dissolution fluid and dissolution fluid attenuating fluid are introduced into the vascular site via the appropriate lumens inside the catheter insert and fluid is removed from the vascular site via the aspiration lumen of the aspiration catheter, and specifically through the annular space present in the system bordered by the inner wall of the aspiration lumen and the outer wall of the catheter insert. The nature of the dissolution fluid and the dissolution fluid attenuating fluid necessarily depends on the nature of the target lesion to be treated. For example, for organic matter comprising lesions, organic matter dissolution fluids (and their companion attenuating fluids) are of interest, such as those described in U.S. patent application Pat. Ser. No. 09/528,576; the disclosure of which is herein incorporated by reference. In other embodiments where the target lesion comprises inorganic matter, acidic dissolution solutions and their companion buffer attenuating fluids are of interest, such as those described in WO 00/03651; the disclosure of the priority document of which is herein incorporated by reference. See e.g., WO 00/03651; WO 01/13985; WO 01/15767; WO 01/39783; WO 01/70320; and WO 02/15958; the disclosures of the priority documents of which are herein incorporated by reference.

In many embodiments, the dissolution fluid employed in the subject methods is an inorganic matter dissolution solution. In many of these embodiments, the inorganic matter dissolution fluid is an acidic dissolution fluid. A variety of different types of acidic dissolution solutions may be employed in the subject methods. The acidic treatment solutions that find use in the subject methods generally have a pH of less than about 6.5, where the pH is usually less than about 4.0 and more usually less than about 3.0. In many preferred embodiments, the pH ranges from 0 to 2, and usually 0 to 1. The acidic treatment solution can include a number of different types of acids, where the acids may or may not include a hydrocarbon moiety, i.e., a hydrogen bonded directly to a carbon atom. Suitable acids that lack a hydrocarbon moiety include halogen acids, oxy acids and mixtures thereof, where specific acids of interest of this type include, but are not limited to, hydrochloric, nitric, sulfuric, phosphoric, hydroboric, hydrobromic, carbonic and hydroiotic acids. For such acids, the acid can be a concentrated acid, or can be diluted. Upon dilution, the concentration of an inorganic acid will generally be from about 10 N to about 0.01 N, preferably between 5 N to 0.1 N. Also of interest are acids that include a hydrocarbon moiety, where such acids include, but are not limited to, any organic acid of one to six ($C_1$ to $C_6$) carbons in length. Organic acids of this type include, but are not limited to, formic, acetic, propionic, maleic, butanoic, valeric, hexanoic, phenolic, cyclopentanecarboxylic, benzoic, and the like. For an organic acid, the acid can be in concentrated form, or can be diluted. The acidic treatment solution can be composed of either a monobasic or a polybasic acid. Acids are "monobasic" when they have only one replaceable hydrogen atom and yield only one series of salts (e.g., HCl). Acids are "polybasic" when they contain two or more hydrogen atoms which may be neutralized by alkalies and replaced by organic radicals.

In many embodiments of the subject invention, the acid solution is hypertonic, by which is meant that the osmolarity of the solution is greater than that of whole blood, i.e. the osomolarity is greater than 300 mosmol. The solution may be rendered hypertonic by including any convenient component or components in the solution that provide for the desired elevated osmolarity.

Any convenient agent that is capable of increasing the osmolarity of the solution may be employed, where suitable agents include salts, sugars, and the like. In many embodiments, the agent that is employed to render the solution hypertonic is one or more, usually no more than three, and more usually no more than two, different salts. Generally, the salt concentration in these embodiments of the solution is at least about 100 mosmol, usually at least about 200 mosmol and more usually at least about 300 mosmol, where the concentration may be as high as 3000 mosmol or higher, depending on the particular salt being employed to render the solution hypertonic, where the solution may be saturated with respect to the salt in certain embodiments. Salts that may be present in the subject solutions include: NaCl, $MgCl_2$, Ringers, etc. where NaCl is preferred in many embodiments.

Of particular interest in many embodiments is the use of a hydrogen chloride solution. In hydrogen chloride solutions that find use in the subject invention, the concentration of HCl in the solution ranges from about 0.001 to 1.0 N, usually from about 0.01 to 1.0 N and more usually from about 0.1 to 1.0 N. In many embodiments, the hydrogen chloride solution will further include one or more salts which make the solution hypertonic, as described above. In certain preferred embodiments, the salt is NaCl, where the concentration of NaCl in the solution is at least 0.05 M, usually at least 0.10 M, and more usually at least 0.15 M, where the concentration may be as high as 0.25 M or higher. In certain embodiments, the solution will be saturated with NaCl.

Of particular interest are aqueous hydrogen chloride solutions that consist of water, hydrogen chloride and NaCl. The concentration of hydrogen chloride in these solutions of particular interest ranges from about 0.01 to 1.0 N, usually from about 0.05 to 0.5 N and more usually from about 0.075 to 0.25 N. The concentration of NaCl in these solutions of particular interest ranges from about 0.05 to 0.25 M, usually from about 0.05 to 0.10 M.

In certain embodiments, one or more of the delivery fluids is present at a temperature that is less than room temperature. For example, in certain embodiments, the one or more treatment solutions, as described above, is present at a temperature ranging from about 0 to about 20° C., sometimes from about 0 to 15° C., e.g., from about 0 to 10° C. Such embodiments include applications where it is desired to limit restinosis by employing reduced temperature, e.g., cold, solutions.

FIG. 6 provides a representation of the distal end of a total occlusion catheter system flushing a target vascular site with an acidic dissolution fluid and a buffer dissolution fluid attenuating fluid. In FIG. 6, the target vascular site 61 is shown with total vascular occlusion 62. The distal end of total occlusion catheter system 60 is shown with aspiration catheter 10 and total occlusion catheter 20 extending beyond the end of aspiration catheter 10. Acidic dissolution fluid 63 exits lumen 25 while buffer dissolution fluid attenuating fluid 64 exits lumen 27. Fluid comprising acid, buffer and dissolved plaque, i.e., 65, is withdrawn from the vascular site by the annular opening of the aspiration lumen of the aspiration catheter.

The target vascular site is flushed with the dissolution and dissolution fluid attenuating fluids for a period of time sufficient to result in the desired amount of treatment, e.g., target lesion size reduction, enhancement or establishment of fluid flow through the target site, etc. Following the desired amount of treatment, the system is removed from the host. More specific detail regarding the methods in which the subject systems find use can be found in U.S. Pat. No. 09/528,576; the disclosure of which is herein incorporated by reference; and publication no. WO 00/03651 the disclosure of the priority document of which is herein incorporated by reference.

In certain embodiments, external energy is applied to the target aortic valve to promote mechanical break-up of the calcified deposits into particles or debris that can be easily removed from the vascular site. Any means of applying external energy to the aortic valve may be employed. As such, jets or other such means the device which are capable of providing varying external forces to the target deposits cause the target deposit to break up or disrupt may be employed. Of particular interest in many embodiments is the use of sonic energy, e.g., ultrasound. Another means that may be employed to apply external energy to the lesion during the dissolution process is to use a mechanical means of applying external energy. Mechanical means of interest include moving structures, e.g. rotating wires, guidewires, which physically contact the target lesion and thereby apply physical external energy to the target lesion.

Kits

Also provided by the subject invention are kits for use in flushing a vascular site with two fluids. The subject kits at least include the components of a partial occlusion or total occlusion catheter system according to the subject invention. As such, the kits include an aspiration catheter and at least one of a partial occlusion catheter and a total occlusion catheter. In many embodiments, the kits include both a partial occlusion catheter and a total occlusion catheter. The subject kits may also include a dissolution fluid and/or dissolution fluid attenuating fluid, or components/precursors thereof, where representative dissolution fluids and dissolution fluid attenuating fluids are disclosed above. The dissolution fluids and dissolution fluid attenuating fluids or component(s) thereof are present in the kit in a suitable container, e.g., a bottle, pouch, fluid filled Endeflator, etc. which is capable of serving as a storage vessel for the this component of the kit and, preferably, capable of preserving the sterility of this component of the kit, as this component of the kit is preferably sterile, e.g., medical grade.

The kits of the subject invention may also include a number of different optional components, which components may find use in methods in which the subject kit components are employed. One optional component that may be present in the subject kits is a guidewire. Any convenient type of guidewire may be present, where a number of different guidewires are known to those of skill in the art. Guidewires of interest include those described in U.S. Pat. Nos. 6,007,514; 5,980,471; 5,957,865; 5,938,609; 5,931,819; 5,916,178; 5,908,395; 5,902,254; 5,865,767; 5,827,201; 5,788,654; 5,772,609; 5,769,796; 5,755,695; 5,749,837; 5,682,897; 5,660,180; 5,636,642; 5,606,981; 5,599,492; 5,596,996; 5,558,093; 5,546,948; 5,520,189; 5,507,301; 5,497,782; D363,776; 5,460,187; 5,441,497; 5,437,288; 5,427,118; 5,421,349; 5,411,033; 5,409,015; 5,368,035; 5,341,818; 5,339,833; 5,313,967; 5,303,714; RE34,466; 5,265,622; 5,238,005; 5,184,621; 5,167,239; 5,147,317; 5,144,959; 5,111,829; 5,107,852; 5,095,915; 5,095,911 5,084,022; 5,069,226; 5,063,935; 4,966,163; 4,953,553; 4,875,489; 4,827,941; 4,811,743; 4,676,249; 4,534,363; 4,080,706 and 4,003,369; the disclosures of which are herein incorporated by reference. Also of interest are dilators for use in creating entries into the vascular system of the host.

Additional optional components that may be present in kits of the subject invention include various fluids and solutions in addition to the dissolution fluid and dissolution fluid attenuating fluid described above. Additional fluids that may be present include: organic matter dissolution fluids, wash or rinsing fluids, imaging agent fluid mediums that include an imaging agent, such as a non-ionic imaging agents, e.g., CONRAY™, OXILAN™, fluids containing one or more pharmacological agents, e.g., agents that promote healing, reduce inflammation, and the like; etc.

Other components that may be present in the subject kits include one or more additional components and accessories for use with the fluid delivery means present in the kit, including tubing for connecting the various catheter components with fluid reservoirs, syringes, pumps, etc., connectors, stop-cocks, dilators, insertion sheaths, vacuum regulators, negative pressure or vacuum generators/sources, luer valve adapters, etc.

In addition to above mentioned components, the subject kits typically further include instructions for using the components of the kit to flush a vascular site with two different fluids, e.g., to flush a vascular site with a dissolution fluid and a dissolution fluid attenuating fluid. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

It is evident from the above discussion that the catheters and systems that are made up of the same provide a reliable and convenient way to flush a target vascular site with two different fluids. Because the catheter devices have a design that allows them to be produced via extrusion technology using polymeric materials, they may be economically produced and the number of different working elements is kept to a minimum. In view of these factors and such others discussed above, the subject kits represent a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Though the invention has been described in reference to a number of examples, optionally incorporating various features, the invention is not to be limited to the set-ups described. The invention is not limited to the uses noted or by way of the exemplary description provided herein. It is to be understood that the breadth of the present invention is to be limited only by the literal or equitable scope of the following claims.

What is claimed is:

1. A system for flushing a vascular site, said system comprising:
   (I) a first two lumen catheter comprising:
      (A) a proximal end;
      (B) a distal end; and
      (C) a three port manifold located at said proximal end, wherein:
         (i) said three port manifold comprises at least two offset ports having luer valves and a central port comprising a Touhy-Borst valve; and
         (ii) said proximal and distal ends are separated by a non-coaxial two lumen tube; and
   (II) a second multilumen catheter inserted inside of one of said two lumens of said first two lumen catheter; wherein said second multilumen catheter is a three lumen catheter comprising:
      (i) a proximal end;
      (ii) a distal end; and
      (iii) a three port manifold located at said proximal end, wherein, each port of said three port manifold comprises a luer valve; and said proximal and distal ends are separated by a non-coaxial three lumen tube.

2. A kit for using in flushing a vascular site with fluid, said kit comprising:
   (I) a first two lumen catheter comprising:
      (A) a proximal end;
      (B) a distal end; and
      (C) a three port manifold located at said proximal end, wherein:
         (i) said three port manifold comprises at least two offset ports having luer valves and a central port comprising a Touhy-Borst valve; and
         (ii) said proximal and distal ends are separated by a non-coaxial two lumen tube; and
   (II) at least one second multilumen catheter comprising a three lumen catheter comprising:
      (i) a proximal end;
      (ii) a distal end; and
      (iii) a three port manifold located at said proximal end, wherein;
         (a) each port of said three port manifold comprises a luer valve; and
         (b) said proximal and distal ends are separated by a non-coaxial three lumen tube.

3. A method for flushing a vascular site with fluid, said method comprising:
   (a) introducing a system according to claim 1 into a patient in a manner such that the distal ends of said multilumen catheters of said system are located at said vascular site; and
   (b) flushing said vascular site with at least one fluid by introducing fluid into and removing fluid from said vascular site through the lumens of said system.

* * * * *